United States Patent [19]

Nies

[11] Plant 4,436

[45] Jul. 10, 1979

[54] CHERRY TREE

[76] Inventor: Marvin L. Nies, 9296 E. Kettleman La., Lodi, Calif. 95240

[21] Appl. No.: 939,900

[22] Filed: Sep. 5, 1978

[51] Int. Cl.[2] ..... A01H 5/03

[52] U.S. Cl. ..... Plt./37

[58] Field of Search ..... Plt./37

*Primary Examiner*—Robert E. Bagwill

*Attorney, Agent, or Firm*—Roger B. Webster

[57] ABSTRACT

A cherry tree which is of medium size and medium vigor, upright to spreading, dense, vase formed, hardy, foliated with large to medium size, ovate occasionally slightly obovate, abruptly to acutely pointed leaves having a crenate, finely serrate margin, and glabrous, opposite-alternate, medium size, mixed, red glands on the petiole adjacent the base of the blade, blooms early from hardy, medium size, medium length, conic, plump, free buds, the resultant flowers being early, medium size, and white, and the tree is a regular and very productive bearer of early-ripening, large to medium size, uniform, symmetrical transversely of the suture plane, globose, semi-freestone fruit having glassy, red skin, and red flesh with lighter streaking radiating from the pit cavity, the latter being red.

3 Drawing Figures

BACKGROUND OF THE VARIETY

1. Field of the Invention

The present variety of cherry tree resulted from a plant breeding program which is conducted by me in my experimental orchard located near Lodi, County of San Joaquin, Calif.; and the purpose of which program is the development of new and distinct varieties of cherry trees especially adapted to commercial growing. The present variety of cherry tree is embraced by Class 37, Plants, of the U.S. Patent Office MANUAL OF CLASSIFICATION.

2. Prior Varieties

Among the existent varieties of cherry trees which are known to me are those mentioned herein; to-wit, Hardy Giant, Bush Tartarian, Burlat, Larian, and Bing.

All of the above varieties are unpatented with the exception of Hardy Giant (U.S. Plant Pat. No. 764).

ORIGIN OF THE VARIETY

The present variety of cherry tree was originated by me, in my experimental orchard located as aforesaid, as a controlled cross of Hardy Giant × Bush Tartarian; the resultant seedling tree, when grown to maturity, evidenced novel and distinctive characteristics, and I, therefore, selected it for asexual reproduction preparatory to ultimate commercial growing thereof.

ASEXUAL REPRODUCTION OF THE VARIETY

The present variety of cherry tree was asexually reproduced by me, in my said experimental orchard, by budding on rootstock, and, in maturity, such asexual reproductions ran true to the original tree in all respects.

SUMMARY OF THE VARIETY

The herein-claimed new and distinct variety of cherry tree is of medium size and medium vigor, upright to spreading, dense, vase formed, hardy, foliated with large to medium size, ovate occasionally slightly obovate, abruptly to acutely pointed leaves having a crenate, finely serrate margin, and glabrous, opposite-alternate, medium size, mixed, red glands on the petiole adjacent the base of the blade, blooms early from hardy, medium size, medium length, conic, plump, free buds, the resultant flowers being early, medium size, and white, and the tree is a regular and very productive bearer of early-ripening, large to medium size, uniform, symmetrical transversely of the suture plane, globose, semi-freestone fruit having glassy, red skin, and red flesh with lighter streaking radiating from the pit cavity, the latter being red.

The herein-claimed new and distinct variety of cherry tree is further characterized as follows:

TREE

The tree, while of moderate vigor, is very healthy, and a lower chilling requirement maintains the tree better in warm winters; the tree, although of medium size, crops early, heavily, and consistently. Further, the tree does not abort fruit during the growing season, as does the Larian for example.

LEAVES

The leaf is more abruptly acuminate than the Larian, as well as being ovate occasionally slightly obovate, whereas Larian has an oval, sharply acuminate leaf. The margin of the leaf is strongly crenate with fine, short teeth; the Larian having coarser dentate teeth which are compound in nature. The petiole is a very light red, while Larian has little pigmentation in the petiole. Pubescence is almost lacking.

FRUIT

The fruit, which is crack-resistant and sizes well (even on cropped trees) is borne—on relatively short stems—heavily and regularly, is uniform in size, ripens evenly, the ripening period being shortly after Burlat but before Larian and Bing, firmer of flesh (with darker red flesh) than Larian but somewhat softer than Bing, and is of an attractive glassy, bright red exterior color which enhances the appearance of the fruit. Additionally, the fruit—which has a good sugar/acid ratio and excellent sweet flavor—generally resembles the Bing in shape, but is slightly more round in cross section and not quite as flattened on the ventral size.

BRIEF DESCRIPTION OF THE DRAWING

The drawing is an illustration, by photographic reproduction in color, of clusters of fruit and leaves on twigs and, separately, detached fruit.

DESCRIPTION OF THE VARIETY

The botanical details of this new and distinct variety of cherry tree—with color definitions (except those in common color terms) referenced to Maerz and Paul Dictionary of Color—are as follows:

Tree:
- *Size.*—Medium.
- *Vigor.*—Medium.
- *Growth.*—Upright — spreading.
- *Density.*—Dense.
- *Form.*—Vase-formed.
- *Hardiness.*—Hardy.
- *Production.*—Very productive.
- *Bearing.*—Regular bearer.

Trunk:
- *Size.*—Medium.
- *Texture.*—Medium.

Branches:
- *Size.*—Medium.
- *Texture.*—Medium.
- *Color.*—Gray. Dull.
- *Lenticels.*—Number — Few. Size — Small.

Leaves:
- *Size.*—Large — medium. Average length — 12.4 cm. Average width — 6.5 cm.
- *Form.*—Ovate — occasionally slightly obovate. Acuminate. Abruptly-acutely pointed.
- *Thickness.*—Thick — medium.
- *Color.*—Top Side — Dark green (23-L-9). Under Side — Lighter green (22-K-7).
- *Texture.*—Smooth.
- *Margin.*—Crenate. Finely serrate.
- *Petiole.*—Medium length. Slender.
- *Glands.*—Glabrous — shiny (new growth). Number — 2-3, sometimes 4. Opposite — alternate (irregular pattern of distribution). Medium size. Mixed. Red. Positioned on petiole adjacent base of blade.
- *Stipules.*—2 — either side of axial bud.

Flower buds:
- *Hardiness.*—Hardy.
- *Size.*—Medium.
- *Length.*—Medium.
- *Form.*—Conic. Plump. Free.

Flowers:
- *Blooming period.*—Mar. 16, 1978. Early, as compared with other varieties.
- *Size.*—Medium.
- *Color.*—White.

Fruit:
- *Maturity when described.*—Eating ripe — May 6, 1978.
- *Date of first picking.*—May 6, 1978.
- *Date of last picking.*—May 15, 1978.
- *Size.*—Uniform. Large — medium. Average diameter axially — 2.5 cm. Average transversely in suture plane — 2.2 cm.
- *Form.*—Uniform. Symmetrical transversely of the suture plane, but asymmetrical in the suture plane. Globose.
- *Suture.*—Shallow. Wide. Extends from base to apex.
- *Ventral surface.*—Rounded slightly.

- *Cavity.*—Flaring — rounded. Elongated in suture plane.
- *Base.*—Rounded. Slightly truncate.
- *Apex.*—Short. Rounded to truncate. Slightly depressed.
- *Pistil point.*—Apical.

Skin:
- *Thickness.*—Medium.
- *Texture.*—Medium.
- *Tenacity.*—Tenacious to flesh.
- *Tendency to crack.*—None in dry season. Resistant to cracking when red ripe.
- *Color.*—Red (8-L-6).
- *Down.*—Wanting.

Flesh:
- *Color.*—Blood red (7-L-6). Surface of Pit Cavity — Dark red.
- *Amygdalin.*—Wanting.
- *Juice.*—Moderate. Rich.
- *Texture.*—Firm — medium. Fine. Meaty.
- *Fibers.*—Few. Fine. Tender.
- *Ripens.*—Evenly.
- *Flavor.*—Subacid.
- *Aroma.*—Wanting.
- *Eating quality.*—Best.

Stone:
- *Type.*—Semi-free.
- *Size.*—Medium. Average length — 1 cm. Average breadth — 8.5 mm. Average thickness — 7 mm.
- *Form.*—Globose. Oval — ovoid.
- *Base.*—Slightly oblique.
- *Hilum.*—Narrow. Oblong.
- *Apex.*—Rounded.
- *Sides.*—Equal.
- *Surface.*—Irregularly furrowed from base to apex ventrally.
- *Ridges.*—Rounded and jagged continuously from base to apex ventrally.
- *Ventral edge.*—Thick, with wing toward base.
- *Dorsal edge.*—Very narrow.
- *Color.*—Beige (13-G-7).

Use: Market — local and long distance.

Keeping quality: Good.

Resistance to insects and diseases: Good.

Shipping quality: Good.

Variance in botanical details: The cherry tree and its fruit herein described may vary in slight detail due to climatic and soil conditions under which the variety may be grown; the present description being of the variety as shown in the Central Valley of California.

I claim:

1. A new and distinct variety of cherry tree, substantially as illustrated and described, characterized, in particular, by large to medium size fruit which is crack-resistant, sizes well, is borne heavily and regularly on relatively short stems, is uniform in size and ripens evenly with the ripening period shortly after Burlat but before Larian and Bing, is firmer with darker red flesh than Larian but softer than Bing, is sweet flavored, and is of an attractive glassy red exterior color; the fruit, in shape, generally resembling the Bing but is slightly more round in cross section and not quite as flattened on the ventral side.

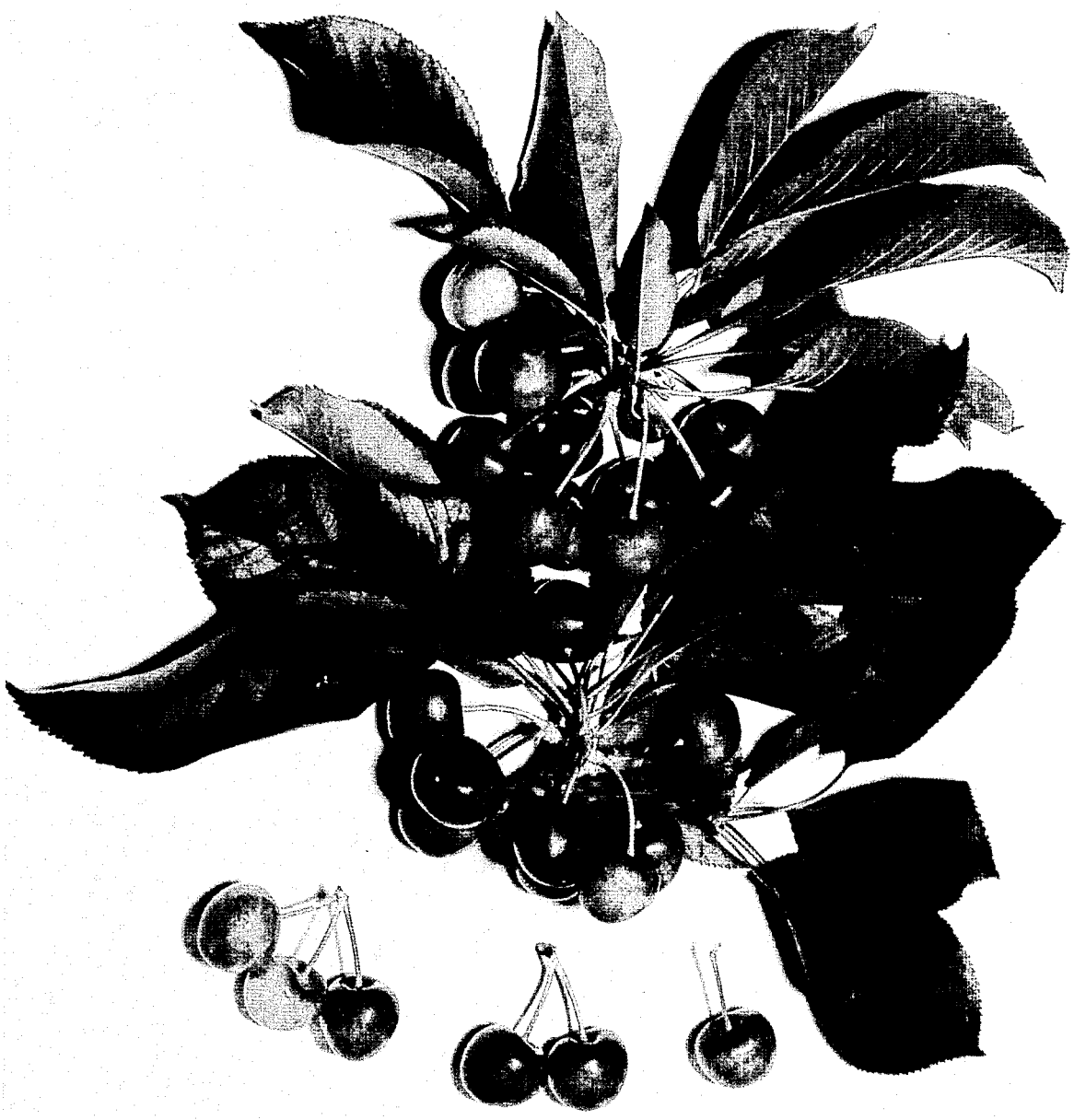

* * * * *